United States Patent [19]
Magin

[11] 3,958,972
[45] May 25, 1976

[54] CHELATES OF 1,2-DIAMINOCYCLOHEXANE TETRAKIS (METHYLENE PHOSPHONIC ACID) USEFUL FOR SUPPLYING NUTRIENT METALS TO PLANTS GROWING IN CALCAREOUS SOIL

[75] Inventor: Ralph W. Magin, Ballwin, Mo.
[73] Assignee: Monsanto Company, St. Louis, Mo.
[22] Filed: July 5, 1974
[21] Appl. No.: 486,270

[52] U.S. Cl. ................................. 71/27; 71/DIG. 2; 260/429 J; 260/438.1
[51] Int. Cl.$^2$ ................... C05C 11/00; C07F 1/08; C07F 1/00
[58] Field of Search ............. 71/27, DIG. 2, 31, 32, 71/33, 64 SC; 260/429 J, 438

[56] References Cited
UNITED STATES PATENTS
2,917,528   12/1959   Ramsey et al. ..................... 260/438

OTHER PUBLICATIONS

Moedritzer et al., Mannich-type Reactions With Orthophosphorous Acid, Journal of Org. Chem. Vol. 31, pp. 1603–1607.
Analytical Chemica Acta Vol. 20 pp. 301–314, "Chelating Properties of N,N,N,N'-tetrakis (phosphonomethyl)–1,2cyclohexane diamine," Banks and Yerick.

*Primary Examiner*—Charles N. Hart
*Assistant Examiner*—Ferris H. Lander
*Attorney, Agent, or Firm*—Thomas B. Leslie

[57] ABSTRACT

Iron, manganese and other essential nutrient metals are supplied to plants growing in calcareous soils by treating the soil with a metal chelating agent or by treating the plant and/or the soil with a metal chelate of said chelating agent, said chelating agent being a 1,2-diaminocyclohexane tetrakis(methylene phosphonic acid) compound.

13 Claims, No Drawings

CHELATES OF 1,2-DIAMINOCYCLOHEXANE TETRAKIS (METHYLENE PHOSPHONIC ACID) USEFUL FOR SUPPLYING NUTRIENT METALS TO PLANTS GROWING IN CALCAREOUS SOIL

BACKGROUND OF THE INVENTION

1. Field of the Invention

This invention relates to chelating agents particularly useful for supplying iron and other essential metals to plants growing in calcareous soils.

2. Description of Prior Art

Many soils encountered in various parts of the world are naturally deficient with respect to the availability of certain trace elements essential to growing plants. This deficiency may result from either an actual depletion of those elements in the soil or from a fixation of the trace elements as insoluble salts or organic complexes which cannot be utilized by the plants. Trace element deficiency, particularly iron deficiency, is commonly associated with alkaline calcareous soils which induce the formation of iron oxide and insoluble iron compounds which are unavailable to plant metabolism. The deficiency of iron results in a condition commonly identified as lime-induced iron chlorosis, a condition wherein the area of the leaf between the veins is a marked yellow green in contrast to the dark green of the veins. Iron chlorosis is often accompanied by a deficiency of other metals such as manganese, zinc and copper which are also essential for healthy plant growth. A discussion of possible causes of lime-induced chlorosis is found in "A Decade of Synthetic Chelating Agents in Inorganic Plant Nutrition," Arthur Wallace, Professor of Plant Nutrition, U.C.L.A. (1962) pages 28–35.

One conventional method of correcting iron deficiency has been simply to apply soluble iron salts such as ferrous sulfate to the soil. Such salts are, however, quickly hydrolyzed in alkaline soils to the oxide or hydroxide forms which are unavailable to the plant.

More recently, more effective results have been obtained by utilizing metal chelating agents to solubilize and maintain metals in a form which can be utilized by the plant. Where the soil actually contains adequate amounts of iron but in an insoluble form, the free chelating agent may be added directly to the soil in order to solubilize the iron and make it available to the plant. Where the soil is actually deficient in iron or other essential metals, metal complexes of the chelating agent may be added to the soil and/or directly onto the foliage of the plant.

Many chelating agents have been suggested to correct metal deficiencies in plants growing in calcareous soils. For example U.S. Pat. No. 3,091,522 suggests carboxylated amines containing a terminal hydroxyl alkyl-sulfoalkyl group.

U.S. Pat. Nos. 2,921,846, 3,005,848, 3,028,407 and 3,248,207 suggest the use of ethylene bis(alpha-imino-o-hydroxyphenylacetic acid) and monoamides thereof.

U.S. Pat. No. 3,472,002 suggests the use of N,N-bis(-disubstituted benzyl)-α-amino acids.

U.S. Pat. Nos. 2,917,528 and 2,964,549 suggest alkanol amino alkane phosphonic acids.

U.S. Pat. No. 3,008,816 suggests alkylene bis-(iminosalicylidene) diphosphonic acid.

U.S. Pat. No. 3,038,793 suggests N,N'-bis(2-hydroxy-5-alkylbenzyl) ethylene diamino diacetic acid.

U.S. Pat. Nos. 3,051,563 and 3,403,992 suggest various carboxylated and/or sulfonated amines such as ethylenediamine tetraacetic acid.

U.S. Pat. No. 2,891,854 suggests the use of diethylene triamine penta(acetic acid).

U.S. Pat. No. 3,463,799 suggests dimethylamino-bis(2-hydroxyphenyl) sulfonic and carboxylic acids.

U.S. Pat. No. 3,131,048 suggests various alpha hydroxy carboxylic acids such as glycolic acid.

British Pat. No. 882,987 suggests various free substituted imino dicarboxylic acids.

The above patents are believed to be representative of the prior art relating to agricultural applications of chelating agents designed to correct metal deficiencies in plants, but those skilled in the art will undoubtedly be aware of yet other patents and references not cited herein. Accordingly, these references are cited for purposes of illustration only and are not to be considered a complete or exclusive list of pertinent references. For example, yet another compound not included in the above patents and which has been suggested as an iron carrier is trans-1,2-diaminocyclohexane tetraacetic acid monohydrate. The iron complex of this compound is reputed to be relatively unaffected by calcareous soils and to not form iron hydroxides.

The chelating agents of the prior art, while for the most part having some beneficial effect when applied to the soil of chlorotic plants, are not completely satisfactory in performance. For example, the ethylene diamine tetraacetic acid chelates of tri- and tetravalent metal ions are unstable in neutral and alkaline solutions and hydrolyze to form insoluble hydroxides in calcareous soils. Other compounds are also either unstable under alkaline conditions or are too expensive to be commercially feasible. Of all the chelating agents of the prior art, the ferric chelate of ethylenediamine di(o-hydroxyphenyl acetic acid) (hereinafter EDDHA) is one of the most effective in overcoming iron deficiency in calcareous soils, and this compound is generally used as a standard in the evaluation of new chelating agents. The use of EDDHA on calcareous soils, however, has the disadvantage of tending to induce low manganese levels in treated plants unless the application of EDDHA is carefully controlled at low levels sufficient to overcome the iron deficiency without promoting a manganese deficiency. This characteristic of EDDHA is discussed in "Comm. in Soil Science and Plant Analysis", 4(1), 51–56 (1973).

It is accordingly an object of the present invention to provide a chelating agent which is useful in supplying nutrient metals to plants growing in calcareous soils. Another object of this invention is to provide metal chelants which are stable to hydrolysis in alkaline soils. It is a further object of this invention to provide a chelating agent which will supply adequate amounts of iron to chlorotic plants without creating a deficiency of other essential metals. These and other objects of this invention will be apparent from the ensuing description.

SUMMARY OF INVENTION

Iron, and other essential nutrient polyvalent metals are supplied to plants growing in calcareous soil by treating the soil with a metal chelating agent or by treating the plant foliage and/or soil with a complex of said polyvalent metal and said chelating agent, said chelating agent being a 1,2-diaminocyclohexane tetrakis(methylene phosphonic acid) of the formula

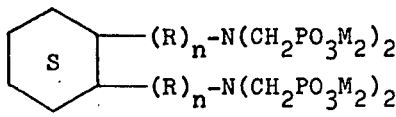

wherein M is hydrogen, alkali metal, ammonium or amine, R is an alkylene or alkylidene radical of from 1 to about 6 and preferably from 1 to 4 carbon atoms and $n$ is 0 or 1. In addition, the cyclohexane ring may be substituted at one or more sites with the substituent which does not adversely affect the performance of the basic compound as set forth above, as, for example, with hydroxyl, $C_{1-4}$ alkali, $-NR_2$, carboxyl, sulfoxy, halogen or other substituent.

The chelating agent may be added to calcareous soils as a free acid, as an alkali metal, ammonium or amine salt or partial salt, or as a metal complex. It may be applied as a dry material or in an aqueous solution, and at concentrations and in amounts effective to prevent or correct the chlorotic condition of plants growing in the calcareous soil.

DESCRIPTION OF PREFERRED EMBODIMENTS

In general, the chelants of the instant invention are utilized as micronutrient carriers for essential nutrient polyvalent metals such as iron, nickel, zinc, manganese, cobalt and copper in accordance with conventional treatment techniques. For the sake of convenience, the following description and discussion will be directed primarily to iron with the understanding that other metals are also included.

Where the soil to be treated contains sufficient iron which is merely in a form unavailable to the plant, the condition of iron chlorosis may be remedied by treatment with free chelant to solubilize the pre-existing iron. The free chelating agent may be applied to the soil surface as a dry powder or as an aqueous solution. It may be applied alone or in conjunction with dry or liquid fertilizers or soil conditioners.

Where the soil to be treated has an actual deficiency of iron or other essential metal, the desired treatment is with a preformed metal chelate which provides the metal in a soluble form which can be utilized by the plant. Metal chelates are readily obtained by dissolving a water soluble metal salt such as ferric chloride and the chelating compound in an aqueous solution. The pH of the solution may be adjusted if desired to maximize stability of the metal chelate. The aqueous metal chelate solution thus formed may be applied according to conventional techniques, e.g., to the soil or to the foliage of the plant or actually injected into the stems or trunks of the plants.

Typical methods for forming metal chelates and treating plants suffering from metal deficiencies are discussed in U.S. Pat. No. 2,921,847 and the methods as set forth therein, particularly in columns 5 through 9, are hereby incorporated by reference as being generally applicable to the instant invention.

The chelating agents of the instant invention are unique as compared to other known chelating agents of the prior art in that treatment of calcareous soils with the iron chelate is effective to prevent iron deficiency in plants which would normally suffer from lime-induced chlorosis without adversely affecting the level of other essential metals in the plant. Specifically, test data has shown that whereas EDDHA is very effective in supplying iron to plants growing in calcareous soils, the treatment with ferric EDDHA may induce low manganese levels in plants. The compounds of the instant invention, on the other hand, correct iron deficiency in chlorotic plants with little or no negative effect on manganese and in some instances actually increase manganese levels in the plant.

The efficacy of the chelating agents of the instant invention are illustrated by tests on the PI 54619-5-1 soybean, a plant particularly susceptible to lime-induced chlorosis in calcareous soils. The use of such plants in screening tests is discussed in "A Decade of Synthetic Chelating Agents in Inorganic Plant Nutrition," Arthur Wallace, Professor of Plant Nutrition, U.C.L.A. (1962) pages 127–131. These tests are conducted by germinating soybean seeds in sand one week before transplanting to a Hacienda loam soil comprising 10% $CaCO_3$, 2.5% organic matter and 28% clay and having a pH of 7.5 and 20 ME/100g cation exchange capacity. Details of the test procedure are as follows.

TEST PROCEDURE

Two soybean seedlings germinated in sand are transferred to 500 grams of dry Hacienda loam soil containing from 100 to 200 ppm nitrogen previously added as ammonium nitrate. Chelated iron compounds in aqueous solution are added to the soil the second or third day after transplanting to provide the particular level of iron desired for testing, usually from 0.5 to 5 ppm based on the 500 gram soil weight. One control sample with zero added iron and a second control with iron added as ferric EDDHA are included for comparative purposes.

The soybean plants are kept in a greenhouse and watered daily or as needed to maintain the soil moisture near saturation. Greenhouse conditions include natural sunlight with daytime temperatures of from 75°–85°F. and minimum nighttime temperatures of 65°F. After a two week growing period, the leaves of each plant are harvested, washed in 0.1N HCl and deionized water, dried at 70°C. in an air circulating oven and weighed to obtain the figure reported as "Leaf Yield". The leaves are then prepared for analysis by grinding in a plastic mill. Powdered leaf material is analyzed for metal content on an Emission Spectrophotometer using conventional procedures. Iron, manganese and other metals are reported as ppm dry weight of leaf material. Similar analytical data can be obtained for the root and stem portions of the plant.

At least four replications of each test condition are run to develop statistically significant data on metal content. Visual response of leaf color from yellow to green is also recorded as an indication of the presence or absence of an iron deficiency. Average values of metal analyses and visual responses for three series of tests evaluating 1,2-diaminocyclohexane tetrakis (methylene phosphonic acid) in comparison with EDDHA are presented in Table I below.

TABLE I

| Chelate | Iron Chelate Mole Ratio Chelate/Fe | Fe ppm | Yield[1] mg | Leaf Analysis Fe ppm | Mn ppm | Leaf Color |
|---|---|---|---|---|---|---|
| Test 1 | | | | | | |
| None | control | | 173 | 31 | 28 | Y |
| DAC[3] | 1:1 | 1 | 203 | 38 | 47 | Y |
| | 1:1 | 2.5 | 238 | 46 | 45 | G |
| | 1:1 | 5 | 289 | 59 | 40 | G |
| EDDHA | 1:1 | 1 | 283 | 84 | 23 | G |
| | 1:1 | 2.5 | 302 | 69 | 14 | G |
| | 1:1 | 5 | 292 | 103 | 14 | G |
| | LSD 0.05[2] | | 42 | 9 | 8 | |
| Test 2 | | | | | | |
| None | control | 4 | 151 | 35 | 37 | Y |
| DAC[3] | 0.5:1 | 4 | 199 | 32 | 58 | G |
| | 1:1 | 4 | 239 | 40 | 41 | G+ |
| EDDHA | 1:1 | 2 | 213 | 49 | 20 | G+ |
| | 1:1 | 4 | 231 | 54 | 19 | G |
| | LSD 0.05 | | 63 | 8 | 14 | |
| Test 3 | | | | | | |
| None | control | | 241 | 38 | 49 | Y |
| DAC[3] | 0.5:1 | 4 | 364 | 37 | 38 | G− |
| | 1:1 | 4 | 351 | 51 | 25 | G |
| EDDHA | 1:1 | 4 | 324 | 55 | 10 | G |
| | LSD 0.05 | | 67 | 12 | 10 | |

[1]Leaf Yield, dry mg. per plant
[2]LSD 0.05 = Least Significant Difference at 95% confidence level
[3]DAC = 1,2-diaminocyclohexane tetrakis(methylene phosphonic acid)

Due to natural variations from week to week in greenhouse environment such as temperature, light and humidity which affect plant growth, comparisons between tests is not considered to be valid and the utilization of the data of Table I should be limited to a comparison between chelating agents and control samples within a test group.

With respect to the tests of Table I, it is apparent that significant improvement over both the zero iron and the EDDHA controls was obtained with the compounds of the instant invention in one or more of leaf yield, leaf iron, leaf manganese or leaf color over the range of iron addition levels evaluated, i.e., from 1 to 5 ppm iron and at Chelate/Iron Mole Ratios as low as 0.5/1.

As compared to the prior art compound EDDHA, the compounds of the instant invention generally provide less iron but more manganese to the plant. The fact that the chelates of the present invention have the ability to provide plants with sufficient iron to prevent iron chlorosis and yet not create manganese deficiencies associated with the use of EDDHA is a surprising and beneficial characteristic of the compounds of the instant invention.

The 1,2-diaminocyclohexane tetrakis(methylene phosphonic acid) chelating agents of the instant invention are prepared by direct synthesis in reacting 1,2-cyclohexane diamine with phosphorus acid and formaldehyde in a Mannich-type reaction. Such reactions are described in detail in an article by Moedritzer and Irani in the Journal of Organic Chemistry, Vol. 31, pages 1603–1607 (1966), and the teachings of this article are incorporated herein by reference.

While the preceding examples and discussions herein have been directed to 1,2-diaminocyclohexane tetrakis(methylene phosphonic acid) as a preferred compound of the present invention, this compound was used for purposes of illustration only and the invention is not to be limited by the limitations of the examples. Specifically, the instant invention encompasses compounds as previously described in Formula I and these compounds may be used with any essential polyvalent metal ion to provide a supply of the metal to growing plants. The compounds are used in "effective amounts", i.e., amounts sufficient to correct the metal deficiency of the plant as determined by analysis or observation. Effective amounts will vary according to the nature of the soil, the type of plant and environmental conditions. Effective amounts for any particular situation are easily determined with a minimum amount of experimentation by testing the chelating compound under actual use conditions. Typically, sufficient metal chelant is used to maintain from about 0.01 to 100 ppm and preferably from about 0.1 to 10 ppm of chelated metal in the soil supporting the plant.

In preparing aqueous solutions of ferric chelate for treating plants via foliage or soil, it is generally preferred that the mole ratio of chelant to iron be within the range of from about 0.5/1 to 2/1. Lower levels of chelant will be partially effective although some unchelated iron may be lost to the plant due to formation of insoluble hydroxides in alkaline soil. Higher levels of chelant can be used with good results especially if some additional iron or other essential metals are available in the soil since the free chelant will solubilize part of these metals and make them available to the growing plant. It should be readily appreciated that in soils actually devoid of metal ions the application of excess free chelant is of little value.

The chelates of this invention may be applied dry or in aqueous solutions, alone or in combination with other chelates, fertilizers, insecticides, fungicides or other plant-treating agents. The chelating agent may be combined with a herbicide for soil application in order to control weeds around the plant being treated. The chelates are useful in correcting a wide range of metal deficiencies in growing plants, particularly iron, nickel, manganese, zinc cobalt and copper deficiencies. Many variations in the method of use will be apparent to those skilled in the art and the invention is accordingly not to be limited except as defined in the claims attached hereto.

The embodiments of this invention in which an exclusive property or privilege is claimed are defined as follows:

1. A method of treating plants which comprises contacting the plant or the soil in which the plant is growing with an effective amount of a chelate of a polyvalent metal and a compound having the formula

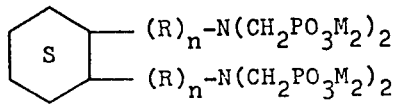

wherein M is hydrogen, alkali metal, ammonium or amine, R is $C_{1-6}$ alkylene or alkylidene and $n$ is 0 or 1.

2. A method of claim 1 wherein from about 0.01 to 100 ppm of said polyvalent metal as said chelate is maintained in the soil supporting the plant.

3. A method of claim 1 wherein the polyvalent metal is selected from the group consisting of iron, nickel, zinc, manganese, cobalt and copper.

4. A method of claim 3 wherein $n$ is 0 and said compound is 1,2-diaminocyclohexane tetrakis(methylene phosphonic acid).

5. A method of claim 3 wherein the mole ratio of said compound to said polyvalent metal is from about 0.5/1 to 2.0/1.

6. A method of claim 1 wherein a plant is treated by applying an aqueous solution of said chelate to the soil supporting said plant.

7. A method of claim 6 wherein the concentration of said polyvalent metal in said aqueous solution is from about 0.01 to 100 ppm.

8. A method of correcting iron deficiency in a plant growing in an alkaline soil which comprises applying a ferric chelate of 1,2-diaminocyclohexane tetrakis(methylene phosphonic acid) to the plant in a quantity effective to correct the iron deficiency.

9. A method of claim 8 wherein the ferric chelate is applied to the foliage of the plant as an aqueous solution.

10. A method of supplying essential metals to plants growing in soil containing insoluble forms of said essential metals which comprises contacting said soil with an effective amount of a compound of the formula

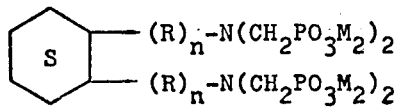

wherein M is hydrogen, alkali metal, ammonium or amine, R is $C_{1-6}$ alkylene or alkylidene and $n$ is 0 or 1.

11. A method of claim 10 wherein said compound is added to the soil as an aqueous solution.

12. A method of claim 10 wherein $n$ is 0 and the compound is 1,2-diaminocyclohexane tetrakis(methylene phosphonic acid).

13. A method of claim 10 wherein said essential metal is selected from the group consisting of iron, nickel, zinc, manganese, cobalt and copper.

* * * * *